United States Patent [19]

Johnson

[11] Patent Number: 4,850,352

[45] Date of Patent: Jul. 25, 1989

[54] LASER-SURGICAL INSTRUMENT WITH EVACUATION TIP

[76] Inventor: Gerald W. Johnson, 821 Peakwood, Houston, Tex. 77090

[21] Appl. No.: 142,182

[22] Filed: Jan. 11, 1988

Related U.S. Application Data

[63] Continuation-in-part of Ser. No. 946,485, Dec. 24, 1986, Pat. No. 4,719,914.

[51] Int. Cl.⁴ .................. A61B 17/36; A61M 1/00
[52] U.S. Cl. ................................. 128/303.1; 604/35
[58] Field of Search ........... 128/303.1, 303.13, 303.14, 128/303.17; 604/35, 902

[56] References Cited

U.S. PATENT DOCUMENTS

| | | | |
|---|---|---|---|
| 3,865,113 | 2/1975 | Sharon et al. | 128/303.1 |
| 3,906,955 | 9/1975 | Roberts | 128/303.17 |
| 3,982,541 | 9/1976 | L'Esperance, Jr. | 128/303.1 |
| 4,503,853 | 3/1985 | Ota et al. | 128/303.1 |

FOREIGN PATENT DOCUMENTS 2549727 2/1985 France ....................... 604/35

*Primary Examiner*—Lee S. Cohen
*Attorney, Agent, or Firm*—Neal J. Mosely

[57] ABSTRACT

A laser surgical instrument is disclosed comprising a laser element mounted in a first hollow tubular member with a tapered open tip for insertion into a surgical site and having an opening at one for connection by a hollow tubing to a source of a purge gas for keeping the laser focusing lens free from smoke. A second tubular member fits on the first tubular member and extends substantially to the first tubular element tapered end. The second tubular member has a side opening for connection to a source of vacuum. A sleeve is slidably mounted on the second tubular member and is movable between a retracted position exposing the tip of the first tubular member and an extended position extending into the surgical site to provide a hood for withdrawal of smoke. The movement of the sleeve between retracted and extended positions provides for selected application of vacuum to the surgical site.

17 Claims, 2 Drawing Sheets

LASER-SURGICAL INSTRUMENT WITH EVACUATION TIP

CROSS REFERENCE TO RELATED APPLICATION

This application is a continuation-in-part of co-pending application Ser. No. 946,485, filed Dec. 24, 1986, now U.S. Pat. No. 4,719,914.

BACKGROUND OF THE INVENTION

1. Field of the Invention

This invention relates to new and useful improvements in laser-surgical instruments and more particularly to an instrument having provision for selective application of vacuum to the surgical site.

2. Brief Description of the Prior Art

Laser-surgical instruments having come into use in recent years as an alternative to electrosurgical instruments which have been in use for about 50 years.

Hyams U.S. Pat. No. 2,102,270 discloses an electrosurgical instrument for female sterilization procedures having an auxiliary tube surrounding the electric blade for introduction of a liquid for radiologically monitoring the operation.

Bierman U.S. Pat. No. 2,275,167 discloses an electrosurgical instrument for removal of tissue by electric current and having means for applying vacuum for drawing in and holding the tissue being cut.

August U.S. Pat. No. 2,808,833 discloses an electrocauterizing instrument with a tube for supplying an inert gas to blanket the surgical site.

Seiger U.S. Pat. No. 2,888,928 discloses an electrocauterizing instrument with a tube for withdrawing blood and smoke from the surgical site by vacuum.

Morrison U.S. Pat. No. 3,828,780 discloses an electrocauterizing instrument with a tube for withdrawing blood and smoke from the surgical site by vacuum and having a side vent opening.

Roberts U.S. Pat. No. 3,906,955 discloses an electrocauterizing instrument with a tube for withdrawing blood and smoke from the surgical site by vacuum and constructed for easy replacement of the blade.

Durden U.S. Pat. No. 3,974,833 discloses an electrocauterizing instrument with a tube for withdrawing blood and smoke from the surgical site by vacuum and having a side vent opening arranged for selective opening and closing to control application of vacuum.

Walker U.S. Pat. No. 4,562,838 discloses an electrocauterizing instrument with a tube for supplying fluid to the surgical site for removing blood and smoke and having a light transmitting cable for illuminating the surgical site.

The prior art as exemplified by these patents and by the instruments now in use in surgery have certain similarities and certain deficiencies in design. All instruments of this type have an electrode for high frequency electro-coagulation. Likewise, most instruments of this type have a tube associated with the blade to either supply a liquid to the surgical site or to aspirate blood and fluid or air (smoke) away from the site. Roberts U.S. Pat. No. 3,906,955 and Walker U.S. Pat. No. 4,562,838 have superficial similarities to this invention and in certain applications work similarly. However these instruments are not as versatile and do not work well in all types of operating conditions. Roberts U.S. Pat. No. 3,906,955 discloses an electro-cauterizing instrument with a tube for withdrawing blood and smoke from the surgical site by vacuum but has a design which provides an inadequate air circulation through the tip for removal of smoke and fluids. Walker U.S. Pat. No. 4,562,838 discloses an electro-cauterizing instrument with a tube for supplying fluid to the surgical site for removing blood and smoke and having a light transmitting cable for illuminating the surgical site, but has an inefficient design of the air flow passages for removal of blood and smoke from the surgical site.

My co-pending application discloses an electrosurgical instrument comprising a hollow tubular member open at one end for connection by a hollow tubing to a source of vacuum and a side opening adjacent to the open end. The opposite end of the tubular member includes a tapered hollow nose portion which may be integral with the tubular member or a separate piece. An electrocauterizing blade is secured in and has one end extending outward from the end of the nose portion and the other end positioned inside the tubular member. Electric heating is provided for the electro-cauterizing blade through an electric lead extending through the tubular member and through the side opening for connection to a power source. The electric heating is usually by application of high frequency current but may be provided by resistance heating. The nose portion has a plurality of openings adjacent to the tapered surface thereof for withdrawing smoke from a surgical area being cut and cauterized by means of vacuum connected to the end of the tubular member. Selectively control of the application of vacuum through the nose portion openings is provided by a tubular sleeve member supported for longitudinal movement on the nose portion to an extended position for selectively covering and uncovering the nose portion openings.

Laser-surgical instruments having come into use in recent years as an alternative to electrosurgical instruments which have been in use for about 50 years. One example of a laser-surgical instrument in current use is the SLT Model CL60 Laser manufactured and sold by Surgical Laser Technologies, Inc., Malvern, Pa. Details of this equipment are available in manufacturer's literature and in the submission for approval by the U.S.F.-D.A. This laser-surgical equipment has a provision for introducing a purge gas to keep smoke away from the focusing lens, but has no provision for evacuating smoke from the site or area of surgery.

SUMMARY OF THE INVENTION

One of the objects of this invention is to provide a new and improved laser-surgical instrument having an evacuation system of more efficient design for removal of blood and smoke from the surgical site.

Another object of the invention is to provide a new and improved laser-surgical instrument having an evacuation system permitting selective application of vacuum during surgery.

Another object of the invention is to provide a new and improved laser-surgical instrument having an arrangement for enclosing the surgical site to force circulation of air through that region by application of vacuum.

Still another object of the invention is to provide a new and improved laser-surgical instrument having a hood or sleeve which is extensible to cause circulation of air through the surgical site and out through discharge openings by application of vacuum to the opposite end of the instrument.

Still another object of the invention is to provide a new and improved laser-surgical instrument having a removable and disposable hood or sleeve for causing circulation of air through the surgical site and out through discharge openings by application of vacuum to the opposite end of the instrument.

Still another object of the invention is to provide a new and improved laser-surgical instrument having a removable and disposable hood or sleeve which is extensible for causing circulation of air through the surgical site and out through discharge openings by application of vacuum to the opposite end of the instrument.

Other objects of the invention will become apparent from time to time throughout the specification and claims as hereinafter related.

The foregoing objects and other objects of the invention are accomplished by a laser surgical instrument is comprising a laser element mounted in a first hollow tubular member with a tapered open tip for insertion into a surgical site and having an opening at one end for connection by a hollow tubing to a source of a purge gas for keeping the laser focusing lens free from smoke. A second tubular member is removably fitted on the first tubular member and extends substantially to the first tubular element tapered end. The second tubular has a side opening for connection to a source of vacuum. A sleeve is slidably mounted on the second tubular member and is movable between a retracted position exposing the tip of the first tubular member and an extended position extending into the surgical site to provide a hood for withdrawal of smoke. The movement of the sleeve between retracted and extended positions provides for selected application of vacuum to the surgical site.

DESCRIPTION OF THE PREFERRED EMBODIMENTS

Figure 1:
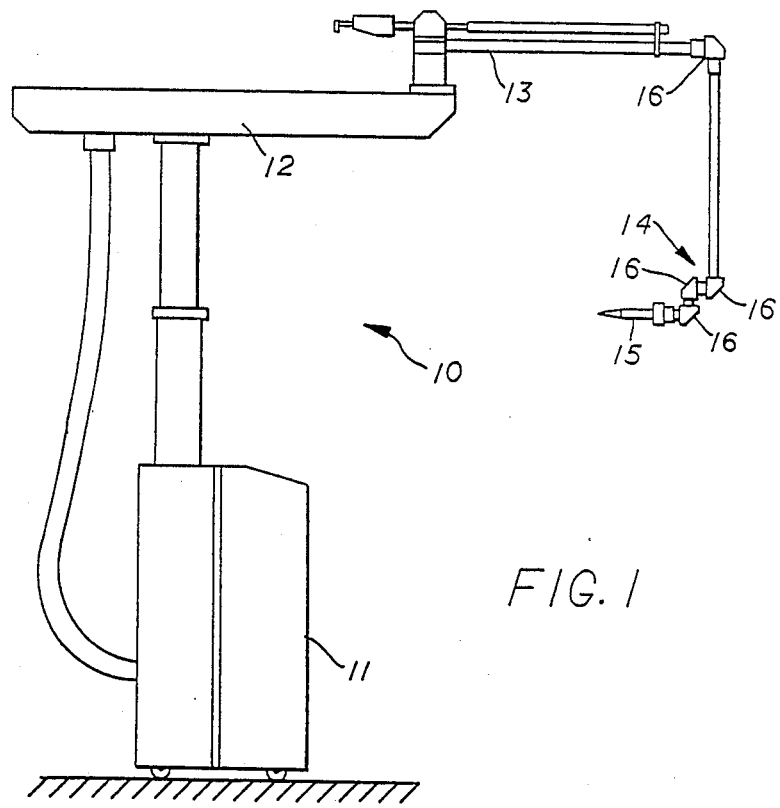
FIG. 1 is a schematic view of a laser-surgical instrument of conventional structure for use with a preferred embodiment of this invention.
Figure 2:
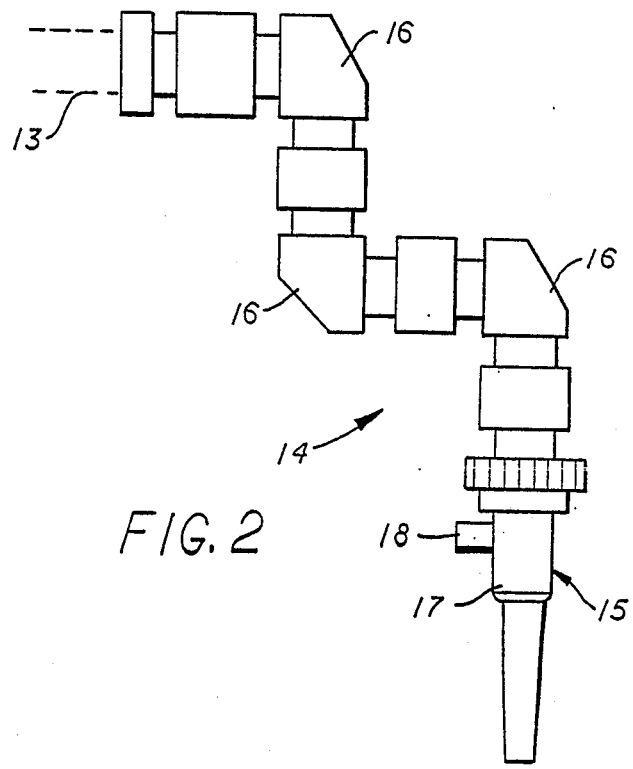
FIG. 2 is view in elevation a focusing head assembly for the instrument shown in FIG. 1 which shows the surgical cutting tip for the instrument.
Figure 3:
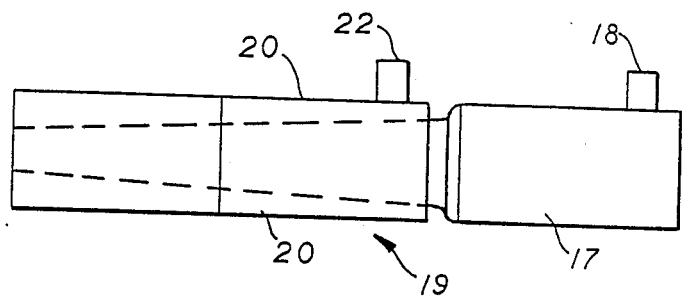
FIG. 3 is view in elevation a removable member for installation on the instrument shown in FIGS. 1 and 2 showing a preferred embodiment of this invention.

Referring to the drawings by numerals of reference, there is shown in FIG. 1 a laser-surgical instrument 10 comprising a wheel-supported base cabinet 11 which contains the circuits for providing suitable power, from an external power source, to a gas-charged laser tube (not shown). The apparatus has a swiveled arm 12 on which there is supported a surgical extension arm 13. Surgical extension arm is connected to a focusing head assembly 14 with surgical tip 15 supported thereon. Focusing head assembly includes mirrors or prisms 16 which transmit the laser beam to the tubular surgical tip 15.

Surgical tip 15 is a hollow, tapered tube 17 through which the laser beam is focused to the surgical site and has a connecting nipple 18 on the side for connection to a source of purging gas (e.g. air, carbon dioxide, nitrogen or helium) which blows through the tube to keep the focusing head clear of smoke. When the apparatus is energized, the laser beam is projected from the laser tube by means of the prisms or mirrors 16 out through the surgical tip 15 to the cutting area. The equipment, as described, is commercially available (an SLC Model 60 Surgical Laser being one type) and is not described in detail since the particular energizing circuits and laser tube, etc. are not critical to the invention claimed herein.

The SLC Model 60 Surgical Laser is a continuous wave Nd:YAG with output at 1.064 microns. It has a maximum power density of 39,000 W./sq. cm. Using 0.2 mm. contact spot size. In the pulse mode, the apparatus is presettable from 0.1 to 10.0 sec. in 0.1 sec. intervals. In the continuous mode, the beam can be of unlimited duration controlled by foot pedal depression (displays up to 99 sec.). Energy measurement for the systems displays 1–9999 joules (resettable) and displays 1–999,999 joules (resettable) cumulative.

The apparatus has an audible laser emitting signal. The aiming beam is helium-neon. The coaxial gas flow (purging gas) is controllable for gas flows of 0.2–1.5 l./min. and for fluid flows of 1–25 ml./min. Sterile, single use fibers are used, as well as non-sterile reusable fibers, for the fiber optics capable of producing spot sizes to 0.2 mm. The equipment is designed with automatic calibration, a fail safe sensing system and has an automatic fiber transmission efficiency display. No external cooling water is required. The apparatus is powered from single phase, 220 V.(+ or −10%), 30 amps., 50–60 Hz. from a dedicated line.

In this type of surgery, the laser beam is focused on small area of tissue to cause ablation, cutting or fusing of the tissue. In eye surgery, where the apparatus has found considerable application, there is not enough vaporization of tissue and tissue by products to cause trouble. However, in laser surgery of other body areas, there is sufficient generation of smoke and vapors to interfere with efficient surgery. There is therefor a substantial need for an efficient means for removal of smoke and vapors during surgery. At present, this has been done by manipulation of a separate aspirator tube which is handled by the surgeon or an assistant and must be coordinated in movement with the surgical tip 15. The present invention provides automatic coordination of movement of the aspirator or suction with the manipulation of surgical tip 15.

Figure 4:
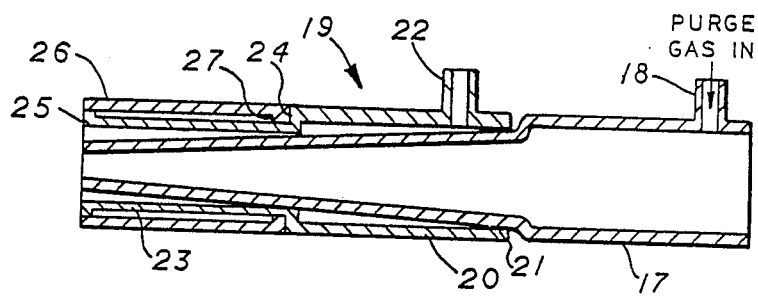
FIG. 4 is view in longitudinal central section of the instrument shown in FIG. 3 with the hood or sleeve in a retracted position.
Figure 5:
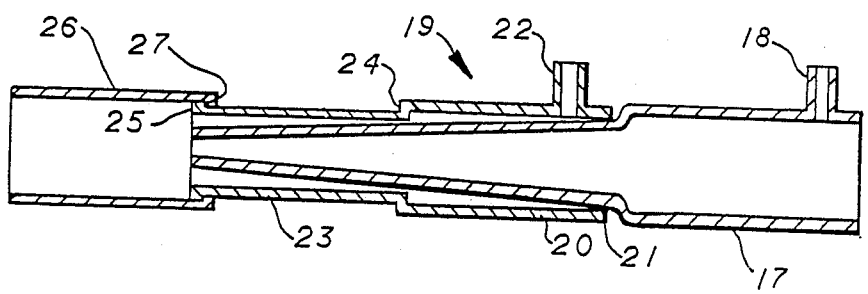
FIG. 5 is view in longitudinal central section of the instrument shown in FIG. 3 with the hood or sleeve in an extended position.

In FIGS. 4 and 5, there is shown a preferred embodiment of the invention in which a removable and controllable evacuation tool 19 is mounted on the tapered portion of surgical tip 15. Evacuation tool 19 comprises a first tubular member 20 having an enlarged end portion 21 which fits tightly and removably on the tapered portion of surgical tip body 17. Enlarged end portion 21 has an inlet nipple 22 for connection to a vacuum line in using the apparatus.

Tubular member 20 has a small end portion 23 with a shoulder 24 at one end and a peripheral flange 25 at the other end. A tubular hood or sleeve 26, with an inturned flange 27 at one end, is slidably positioned on small end portion 23 abutting stop shoulder 24 in the retracted position and has an inturned flange 27 which abuts stop flange 25 in the extended position.

OPERATION

The laser surgical instrument 10 is used in surgical operations as described above. Evacuation tool 19 is mounted on the tapered portion of surgical tip 15 as described above. The surgical tip 15 has nipple 18 connected to a source of purge gas (air, carbon dioxide, nitrogen or helium) and evacuation tool has nipple 22 connected to vacuum, both connections being by suitable tubing (not shown).

The apparatus is energized by means of a foot control switch (not shown) and the laser emits a coherent beam of light (laser beam) which is transmitted to the surgical site by the prisms or mirrors 16. The laser beam burns the tissue in a very small area with generation of a substantial amount of smoke and vapors.

When the hood or sleeve 26 is retracted, surgical tip 15 is exposed for surface surgery with the purge gas supplied through inlet nipple 18 keeping the focusing head clear. When the hood or sleeve 26 is fully extended (stop flanges 25 and 27 keep it from coming off), vacuum applied through inlet nipple 22 draws smoke and vapors out of the surgical site. Evacuation tool 19, i.e., tube 20 and hood or sleeve 26, is preferably formed of optically clear plastic which does not interfere with the surgeons view of the operation when the hood sleeve 26 is extended in use.

Much of this advantage arises from the use of the extended sleeve or hood 26 which moves the region of suction into the surgical site. It is not possible to use a fixed, extended sleeve or hood because of problems of sanitation required in surgery. When an extensive operation is carried out, fat and tissue are carbonized to a residue which may clog the cutting tip much as carbonized fats stick to and encrust a cooking grill. The cutting tip should be cleaned frequently by scraping away the carbonized organic materials. This cleaning cannot be done if a fixed, extended sleeve or hood is used. The use of the retractable sleeve or hood 26 therefore performs the dual function of increasing the suction adjacent to the cutting tip and, on retraction, permits the cleaning of the surgical tip 15.

While this invention has been described fully and completely, with special emphasis on the preferred embodiments, it should be understood that, within the scope of the appended claims, the invention may be practiced otherwise than as specifically described herein.

I claim:

1. A laser-surgical instrument comprising, in combination:
    a hollow tubular surgical tip having an opening at one end connectable to a laser beam generator for receiving a laser beam projectable therethrough to a surgical site at an open other end thereof,
    said surgical tip having an inlet nipple for connection to a source of a purge gas to keep a focusing head free of smoke and vapors during use, and
    an evacuation tool comprising
    a tubular member open at both ends and having one end removably fitted tightly on said surgical tip with a small clearance between said tubular member and surgical tip between the region of tight fit and the respective other ends of said tubular member and said surgical tip,
    said tubular member having an inlet nipple for connection to a source of vacuum, and
    means on said tubular member for effectively extending said other end thereof substantially beyond said other end of said surgical tip for application of vacuum inside the surgical side during use.

2. A laser-surgical instrument according to claim 1 in which
    said means for extending said other end of said tubular member comprises an extension sleeve slidably mounted thereon.

3. A laser-surgical instrument according to claim 2 in which
    said tubular member has a larger diameter portion at said one end having said tight fit on said surgical tip, and a smaller diameter portion at said other end with a stop shoulder therebetween, and
    said extension sleeve being slidably mounted on said smaller diameter portion.

4. A laser-surgical instrument according to claim 2 in which
    said tubular member has a larger diameter portion at said one end having said tight fit on said surgical tip, and a smaller diameter portion at said other end with a stop shoulder therebetween and a stop flange at said other end,
    said extension sleeve being slidably mounted on said smaller diameter portion and having an inturned stop flange,
    said extension sleeve having a retracted position abutting said stop shoulder and an extended position with said stop flanges abutting to prevent removal of said sleeve from said tubular member.

5. A laser-surgical instrument according to claim 2 in which
    said surgical tip has an enlarged body portion and a tapered tubular portion extending therefrom,
    said tubular member has a larger diameter portion at said one end having said tight fit on the larger end portion of said tapered surgical tip, and a smaller diameter portion at said other end with a stop shoulder therebetween,
    the clearance between said tubular member and the tapered surface of said surgical tip tapered portion providing a passage for gas flow from the open other ends of said tubular member and surgical tip to said inlet nipple to be connected to vacuum, and
    said extension sleeve being slidably mounted on said smaller diameter portion.

6. A laser-surgical instrument according to claim 2 in which
    said surgical tip has an enlarged body portion and a tapered tubular portion extending therefrom,
    said tubular member has a larger diameter portion at said one end having said tight fit on the larger end portion of said tapered surgical tip, and a smaller diameter portion at said other end with a stop shoulder therebetween, and a stop flange at said other end,
    the clearance between said tubular member and the tapered surface of said surgical tip tapered portion providing a passage for gas flow from the open other ends of said tubular member and surgical tip to said inlet nipple to be connected to vacuum,
    said extension sleeve being slidably mounted on said smaller diameter portion and having an inturned stop flange, and
    said extension sleeve having a retracted position abutting said stop shoulder and an extended position with said stop flanges abutting to prevent removal of said sleeve from said tubular member.

7. A laser-surgical instrument according to claim 2 in which
said tubular member and extension sleeve are each of optically clear plastic.

8. A laser-surgical instrument according to claim 2 in which
said tubular member and extension sleeve are each of optically clear plastic,
said tubular member has a larger diameter portion at said one end having said tight fit on said surgical tip, and a smaller diameter portion at said other end with a stop shoulder therebetween, and
said extension sleeve being slidably mounted on said smaller diameter portion.

9. A laser-surgical instrument according to claim 2 in which
said tubular member and extension sleeve are each of optically clear plastic,
said tubular member has a larger diameter portion at said one end having said tight fit on said surgical tip, and a smaller diameter portion at said other end with a stop shoulder therebetween and a stop flange at said other end,
said extension sleeve being slidably mounted on said smaller diameter portion and having an inturned stop flange,
said extension sleeve having a retracted position abutting said stop shoulder and an extended position with said stop flanges abutting to prevent removal of said sleeve from said tubular member.

10. An evacuation tool for use with a laser-surgical instrument comprising:
a hollow tubular surgical tip having an opening at one end connectable to a laser beam generator for receiving a laser beam projectable therethrough to a surgical site at an open other end thereof,
said surgical tip having an inlet nipple for connection to a source of a purge gas to keep a focusing head free of smoke and vapors during use,
said evacuation tool comprising
a tubular member open at both ends and having one end adapted to be removably fitted tightly on said surgical tip with a small clearance between said tubular member and surgical tip between the region of tight fit and the respective other ends of said tubular member and said surgical tip,
said tubular member having an inlet nipple for connection to a source of vacuum, and
means on said tubular member for effectively extending said other end thereof substantially beyond said other end of said surgical tip when installed thereon for application of vacuum inside the surgical site during use,
said means for extending the open end of said tubular member comprising an extension sleeve slidably mounted thereon.

11. An evacuation tool for a laser-surgical instrument according to claim 10 in which
said tubular member has a larger diameter portion at said one end adapted to have said tight fit on said surgical tip, and a smaller diameter portion at said other end with a stop shoulder therebetween, and
said extension sleeve being slidably mounted on said smaller diameter portion.

12. An evacuation tool for a laser-surgical instrument according to claim 10 in which
said tubular member has a larger diameter portion at said one end adapted to have said tight fit on said surgical tip when installed thereon, and a smaller diameter portion at said other end with a stop shoulder therebetween and a stop flange at said other end,
said extension sleeve being slidably mounted on said smaller diameter portion and having an inturned stop flange,
said extension sleeve having a retracted position abutting said stop shoulder and an extended position with said stop flange abutting to prevent removal of said sleeve from said tubular member.

13. An evacuation tool for a laser-surgical instrument according to claim 10 for use with a surgical tip having an enlarged body portion and a tapered tubular portion extending therefrom, in which
said tubular member has a larger diameter portion at said one end having said tight fit on the larger end portion of said tapered surgical tip portion when installed thereon, and a smaller diameter portion at said other end with a stop shoulder therebetween,
the clearance between said tubular member and the tapered surface of said surgical tip tapered position when installed thereon providing a passage for gas flow from the open other ends of said tubular member and surgical tip to said inlet nipple to be connected to vacuum, and
said extension sleeve being slidably mounted on said smaller diameter portion.

14. An evacuation tool for a laser-surgical instrument according to claim 10 for use with a surgical tip having an enlarged body portion and a tapered tubular portion extending therefrom, in which
said tubular member has a larger diameter portion at said one end having said tight fit on the larger end portion of said tapered surgical tip portion when installed thereon, and a smaller diameter portion at said other end with a stop shoulder therebetween, and a stop flange at said other end,
the clearance between said tubular member and the tapered surface of said surgical tip tapered portion when installed thereon providing a passage for gas flow from the open other ends of said tubular member and surgical tip to said inlet nipple to be connected to vacuum,
said extension sleeve being slidably mounted on said smaller diameter portion and having an inturned stop flange, and
said extension sleeve having a retracted position abutting said stop shoulder and an extended position with said stop flanges abutting to prevent removal of said sleeve from said tubular member.

15. An evacuation tool for a laser-surgical instrument according to claim 10 in which
said tubular member and extension sleeve are each of optically clear plastic.

16. An evacuation tool for a laser-surgical instrument according to claim 10 in which
said tubular member and extension sleeve are each of optically clear plastic,
said tubular member has a larger diameter portion at said one end adapted to have said tight fit on said surgical tip when installed thereon, and a smaller diameter portion at said other end with a stop shoulder therebetween, and
said extension sleeve being slidably mounted on said smaller diameter portion.

17. An evacuation tool for a laser-surgical instrument according to claim 10 in which
said tubular member and extension sleeve are each of optically clear plastic,
said tubular member has a larger diameter portion at said one end adapted to have said tight fit on said surgical tip when installed thereon, and a smaller diameter portion at said other end with a stop shoulder therebetween and a stop flange at said other end,
said extension sleeve being slidably mounted on said smaller diameter portion and having an inturned stop flange,
said extension sleeve having a retracted position abutting said stop shoulder and an extended position with said stop flanges abutting to prevent removal of said sleeve from said tubular member.

* * * * *